(12) United States Patent
Granik et al.

(10) Patent No.: US 8,440,670 B2
(45) Date of Patent: May 14, 2013

(54) PYRIDOPYRAZINDIONE DERIVATIVE AND ITS USE AS AN ANTIULCER DRUG

(75) Inventors: Vladimir Grigorevich Granik, Moscow (RU); Valeriya Markovna Ljubchanskaya, Moscow (RU); Valery Aleksandrovich Parshin, Moscow (RU); Marina Alekseevna Kalinkina, Moscow (RU)

(73) Assignee: Innovative Pharmacology Research OOO (IPHAR), Tomsk (RU)

( * ) Notice: Subject to any disclaimer, the term of this patent is extended or adjusted under 35 U.S.C. 154(b) by 0 days.

(21) Appl. No.: 13/602,239

(22) Filed: Sep. 3, 2012

(65) Prior Publication Data
US 2012/0329804 A1 Dec. 27, 2012

Related U.S. Application Data

(63) Continuation of application No. PCT/RU2011/000103, filed on Feb. 28, 2011.

(30) Foreign Application Priority Data

Mar. 5, 2010 (RU) ................................ 2010107989

(51) Int. Cl.
*A61K 31/4985* (2006.01)
*A61P 1/04* (2006.01)
*C07D 471/04* (2006.01)

(52) U.S. Cl.
USPC ............................ 514/249; 514/250; 544/349

(58) Field of Classification Search .................. 514/249, 514/250; 544/349
See application file for complete search history.

(56) References Cited

U.S. PATENT DOCUMENTS
7,041,704 B2 * 5/2006 Burgard et al. ............... 514/727

FOREIGN PATENT DOCUMENTS
SU 241446 A1 4/1969
WO 2005030214 A1 4/2005

OTHER PUBLICATIONS

Lubchanskaya, et al, Academy of Sciences Izv., chem.., 2002, pp. 1736-1743, No. 10.
El-Matary et al., "Omeprazole-Induced Hepatitis", Pediatric Emergency Care, Aug. 2005, pp. 529-530, vol. 21, No. 8.
Raghunath et al., "Review article: the long-term use of proton-pump inhibitors", Aliment Pharmacol. Ther., 2005, pp. 55-63, vol. 22, Suppl. 1.
Reilly, "Safety profile of the proton-pump inhibitors", Am. J. Health-Syst. Pharm., Dec. 1, 1999, pp. S11-S17, vol. 56, Suppl. 4.
Clissold et al., "Omeprazole: A Preliminary Review of its Pharmacodynamic and Pharmacokinetic Properties, and Therapeutic Potential in Peptic Ulcer Disease and Zollinger-Ellison Syndrome", 3 pages, 1986.
Katz et al., "Rioprostil Heals Pre-Existing Aspirin-Induced Gastric Lesions in Dogs During Daily Aspirin Administration Without Altering the Anti-inflammatory or Analgesic Efficacy of Aspirin", The Journal of Pharmacology and Experimental Therapeutics, 1989, pp. 774-781, vol. 251, No. 2.
Esplugues et al., "Role of Nitric Oxide in Gastric Functions", Meth Find Exp Clin Pharmacol, 1997, pp. 25-27, vol. 19, Suppl. A.
Cuzzolin et al. "Role of endogenous and exogenous nitric oxide on intestinal mucosa and microflora in the rat", Inflammation, 1997, pp. 443-450, vol. 21, No. 4.
Yoshimura-Mishima et al., "Suppressive Effect of Oren-gedoku-to (Huang-Lian-Jie-Du-Tang) on the Production of Superantigen by *Staphylococcus aureus*", Japanese Pharmacology & Therapeutics, 2002, p. 225-230, vol. 30, No. 3.
Huang et al., "Pharmacological and pharmacodynamic essentials of H2-receptor antagonists and proton pump inhibitors for the practising physician", Best Practice & Research Clinical Gastroenterology, 2001, pp. 355-370, vol. 15, No. 3.
Hayashi et al., "Inhibitory Action of Oren-gedoku-to Extract on Enzymatic Lipid Peroxidation in Rat Liver Microsomes," Biol. Pharm. Bull., Oct. 2001, pp. 1165-1170, vol. 24, No. 10.
Vagin O. et al., "SCH28080, a K+-Competitive Inhibitor of the Gastric, H,K-ATPase, Binds Near the M5-6 Luminal Loop, Preventing K+ Access to the Ion Binding Domain", Biochemistry, 2002, pp. 12755-12762, vol. 41, No. 42.
Saha et al., "Enhanced Gastroprotective and Anti-Ulcerogenic Activities in Rats of a New Class of Proton Pump Inhibitor Containing Nitrosothiol Nitric Oxide Donor", pp. A-144-A-145, Abstract #772, 2001.
Yano et al., "Antiulcer Activities of Glycyrrhetinic Acid Derivatives in Experimental Gastric Lesion Models", Chem. Pharm. Bull., 1989, pp. 2500-2504, vol. 37, No. 9.
Derelanko et al., "Carbenoxolone Sodium Protects Rat Gastric Mucosa against Ethanol-Induced Necrosis (41080)", Proceedings of the Society for Experimental Biology and Medicine, 1981, pp. 394-397, vol. 166.
Ohta et al., "Protective Effect of Teprenone Against Acute Gastric Mucosal Lesions Induced by Compound 48/80, a Mast Cell Degranulator, in Rats", Journal of Pharmacological Sciences, 2003, pp. 337-346, vol. 93.
Shay et al. "A Simple Method for the Uniform Production of Gastric Ulceration in the Rat", Uniform Production of Gastric Ulceration, 1945, pp. 43-61, vol. 5.
Janssen et al., "Research Papers A New Series of Potent Analgesics: dextro 2: 2-diphenyl-3-methyl-4-morpholino-butyrylpyrrolidine and related amides", pp. 381-400, 1957.
Belensky, M.L., "Elements of Quantitative Evaluation of Pharmacological Effect," 1963, pp. 70-85, Leningrad.
Kaminski J. et al., "Antiulcer Agents. 5. Inhibition of Gastric H+/K+-ATPase by Substituted Imidazo[1,2-a]pyridines and Related Analogues and Its Implication in Modeling the High Affinity Potassium Ion Binding Site of the Gastric Proton Pump Enzyme," J. Med. Chem., 1991, pp. 533-541, vol. 34, No. 2.
Sachs G. et al., "The Gastric H,K ATPase as a Drug Target: Past, Present, and Future", J. Clin. Gastroenterol., Jul. 2007, pp. S226-S242, vol. 41, Suppl. 2.
International Search Report dated Aug. 4, 2011 for corresponding International Application No. PCT/RU2011/000103 filed Feb. 28, 2011.

* cited by examiner

*Primary Examiner* — Renee Claytor
*Assistant Examiner* — Sahar Javanmard
(74) *Attorney, Agent, or Firm* — Patentbar International P.C.

(57) ABSTRACT

The invention relates to the fields of the chemical and pharmaceutical industry and medicine and concerns a novel compound which can be used as an antiulcer agent. The compound is 9-(quinony-2)-2-p-ethoxyphenylethyl-4,5,6,7,8,9,10,11-octahydropyrido [1,2-a]pyrazindione-1,4 of formula (I), or pharmaceutically acceptable complex derivatives thereof. The compound can be used as an antiulcer agent.

6 Claims, No Drawings

PYRIDOPYRAZINDIONE DERIVATIVE AND ITS USE AS AN ANTIULCER DRUG

RELATED APPLICATIONS

This application is a Continuation application of International Application PCT/RU2011/000103, filed on Feb. 28, 2011, which in turn claims priority to Russian Patent Applications No. RU 2010107989, filed Mar. 5, 2010, both of which are incorporated herein by reference in their entirety.

FIELD OF THE INVENTION

The present invention relates to the fields of the chemical and pharmaceutical industry and medicine and concerns a novel compound which can be used as an antiulcer agent.

BACKGROUND OF THE INVENTION

Gastrointestinal (GI) tract diseases were always central to medical concern due to their high prevalence. Of many diseases of this group gastric ulcers and duodenal ulcers have special social and medical significance, because their prevalence exceeds the prevalence of all other GI tract pathologies.

Medical treatment of peptic ulcer disease (PUD) aims to reduce the damaging effects of gastric acid (antisecretory drugs) on gastric tissues, raise the resistance of affected tissues, foremost of all gastric mucosa (gastroprotective drugs), and combat *Helicobacter Pylori* microorganisms (antimicrobial therapy).

The primary type of antiulcer treatment is periodic or sustained therapy using antisecretory drugs: proton pump inhibitors, histamine $H_2$-receptor antagonists, antacid drugs, bismuth drugs (bismuth subsalicylate/subcitrate), sucralfate (a combination of aluminium hydroxide and sucrose octasulfate). Histamine $H_2$-receptor antagonists, popular in the 1980s, have largely been superseded by more effective antisecretory drugs—proton pump inhibitors.

Proton pump inhibitors (PPIs) were first synthesized in 1976. The first PPIs were timoprazole and omeprazole. Timoprazole fell into obscurity, while omeprazole achieved widespread medical recognition. In 1988 Omeprazole was officially recommended for clinical use at the World Congress of Gastroenterology in Rome. One of the reasons for such recognition was the proof of its high efficacy in eliminating *Helicobacter pylori* (HP) bacteria, the discovery of which in 1983 has forced the medical community to review the nature of gastro duodenal diseases. *Helicobacter* infection received great attention because WHO experts recognized it as carcinogenic for humans after extensive research. That made the problem of HP eradication in gastric mucosa (and providing optimal conditions for ulcer healing) extremely important.

Despite omeprazole's widespread recognition and use as the first effective PPI, efforts to improve it continued. In 1992 specialists of Japanese firm Takeda have synthesized a new-generation PPI—lansoprazole. After a few years next-generation PPIs have appeared: pantoprazole, rabeprazole, esomeprazole.

Currently IPPs are the most widely used gastroduodenal ulcer treatment drugs in the world.

PPIs have been used for PUD treatment for over 15 years, however, their safety is not fully established. Dangerous adverse effects or life threatening PPI interactions with other drugs sometimes may be discovered only after extensive use—hundreds of thousands uses may be required. However, even now adverse effects of PPI (mainly omeprazole) on liver are documented in children [1]. Clinical use has also shown other adverse effects: diarrhea, nausea, abdominal colic, drowsiness, and headaches.

Long-term use of omeprazole and other PPIs (as well as some other antisecretory drugs) may lead to a potent and prolonged inhibition of gastric secretion and sometimes atrophy of gastric secretory cells, causing severe complications (development of tumors like gastrinoma, adenocarcinoma, *Helicobacter Pylori* infestation, intestinal infections, intestinal malabsorption of fats, minerals and vitamins). All of these complications are described in the following literature: [2]. In addition, it should be taken into account that PPI metabolism involves cytochrome P450 oxidase system, so long-term PPI use may cause tolerance to such drugs after this enzyme system's activity is exhausted [3]. This may be connected to the known withdrawal syndrome—relapse of the disease after some time (from 2 to 22 weeks, average 14 weeks) of omeprazole cancellation [4].

Other adverse and undesirable effects are known in drugs of this class, which are usually shown in indications for use (headache, diarrhea, allergy, gynecomastia, etc).

PPIs are thus quite effective drugs, widely used in PUD treatment, however they also have adverse effects and negative consequences (the most dangerous of them, possibly lethal, is infestation by *Helicobacter pylori* and tumor development). Also, they are sometimes ineffective in treatment. This makes the search for new antiulcer drugs important and relevant.

The most promising venue of new antiulcer drug development is synthesizing a drug with gastroprotective properties, as this does not cause "hard" inhibition of gastric secretion. The latter causes the main adverse effects—*Helicobacter pylori* infestation and tumor processes Inhibition may be undesirable, when secretion levels are normal or low, which is frequently encountered during PUD. In such case all that is needed is to "protect" gastric mucosa from irritation, so that the damaged mucosa was not further damaged by acid, but instead protected from it.

Such drugs are usually based on prostaglandins. Prostaglandins stimulate mucus secretion and activate protein kinase, which, by acting on cell membrane, can protect gastric mucosa from aggressive effects of acid and pepsin. On the other hand, prostaglandins can inhibit gastric acid secretion. This combined action makes prostaglandins very promising antiulcer drugs, however, there is little experience of their use, currently they are only at clinical trials stage [5].

Another promising venue is the development of gastroprotective drugs—NO donors. Nitric oxide acts as a multifunctional gastroprotective mediator, affecting some aspects of GI tract action, including bile and bicarbonate secretion and blood flow in GI tract walls [6]. NO also possesses antimicrobial properties, in particular towards *Helicobacter pylori* bacteria [7]. NO donors do not have direct antisecretory effect, but bicarbonate, secreted under their influence in stomach, interacts with gastric acid, neutralizing it.

Other drugs are used to inhibit gastric acid secretion: $H_2$-receptor antagonists (famotidine, ranitidine, cimetidine) and proton pump inhibitors. $H_2$-receptor antagonists have significant drawbacks compared to PPIs: a) they block only the signal created during histamine binding, b) their action is reversible and they eliminate quickly from the bloodstream, forcing a patient to take several pills a day. Their use also leads to intense histamine receptor synthesis, causing "rebounds" of HCL secretion after their cancellation.

The first proton pump inhibitor in the market was omeprazole (AstraZeneca), a substituted benzimidazole which appeared in the 80s. PPIs currently present in the market are also substituted benzimidazoles. They are: nexium (S-enantiomer of omeprazole or esomeprazole, AstraZeneca), multiple omeprazole generics, pariet (rabeprazole, Janssen-Cilag) and controloc (pantoprazole, Byk Gulden, not sold in Russia). All these compounds are prodrugs. They are weak bases, and being exposed to the acidic environment of parietal vesicles they bind $H^+$ and undergo molecular transformation into the drug—an active sulfenamide interacting with SH-groups of H-ATPase in secretory vesicle. Sulfenamides form covalent bond with SH groups, so their action is irreversible. Their action stops only after the elimination of H-ATPase molecule, modified by an inhibitor, and half-life of H,K-ATPase in humans is about 40 hours. This makes second-generation PPIs like pariet and nexium highly effective in treating acid-dependent diseases. PUD treatment using these inhibitors combined with antibiotics, eliminating *Helicobacter pylori* infection, is effective in 90% of cases [20].

In addition to irreversible proton pump inhibitors, reversible inhibitors also exist, however there are currently no drugs based on them. This is probably due to very high efficacy and safety of irreversible PPIs.

Among reversible PPIs the most well-known one is imidazopyridine SCH-28080 which inhibits H,K-ATPase by $K^+$-competitive mechanism with $K_i$ (inhibition constant) of 0.2-0.24 µmol [21].SCH-28080 analogs interact with a fragment of H,K-ATPase's 44 amino-acid residues long a-subunit, starting with Leu-854 and ending with Arg-897. This fragment is homologous to the one of H,K-ATPase, which SCH-28080 also inhibit, but with less affinity. Apparently it represents the K-binding center of these related enzymes. Besides SCH-28080 other more specific inhibitors are known—SK&F that inhibits only H,K-ATPase with 0.5 µmol and competes with SCH-28080 and $K^+$ and SK&F96356 that inhibits H,K-ATPase with $K_i$=0.07 µmol, also competing with SCH-28080 and $K^+$.

The drug SCH 28080 with a formula:

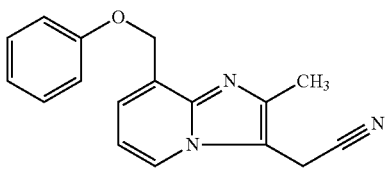 [SMILES: Cc1nc2c(COc3ccccc3)cccn2c1CC#N]

can be considered the closest analog [19]. The compound is effective, however competitive action to $K^+$ ions is possible, which can lead to negative adverse effects.

SUMMARY OF INVENTION

The goal of this invention is the creation of an antiulcer compound with potent antiulcer activity and lacking adverse effects of the known drugs.

The goal is achieved by synthesizing a new compound—a pyridopyrazindione derivative. The invention proposes a compound 9-(quinonil-2)-2-p-ethoxyphenylethyl-4,5,6,7,8,9,10,11-octahydropyrido[1,2-a]pyrazindione-1,4 of formula (I) and its pharmaceutically acceptable complex derivatives.

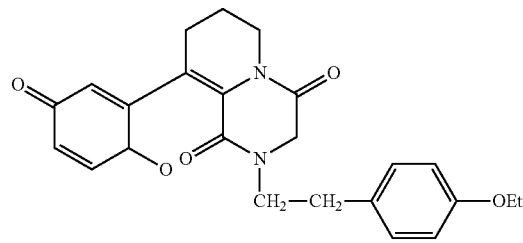

DETAILED DESCRIPTION OF THE PREFERRED EMBODIMENTS

Synthesis of the Compound I

The parent substance for synthesis is a chromene derivative (II) which is converted by chloroacetyl chloride to the corresponding chloroacetyl derivative (III).

The action on the latter of β(p-ethoxyphenyl)ethylamine have caused the opening of pyran cycle and formation of piperazinedione ring. Subsequent oxidation of hydroquinone fragment in the intermediate IV have led to the formation of compound I. (Synthesis of chromene II is described by us in the paper: B. M. Lubchanskaya, L. M. Alexeeva, S. A. Savina, A. S. Shashkov, V. G. Granik, Academy of Sciences Izv., chem.., 2002, N10, p. 1736-1743).

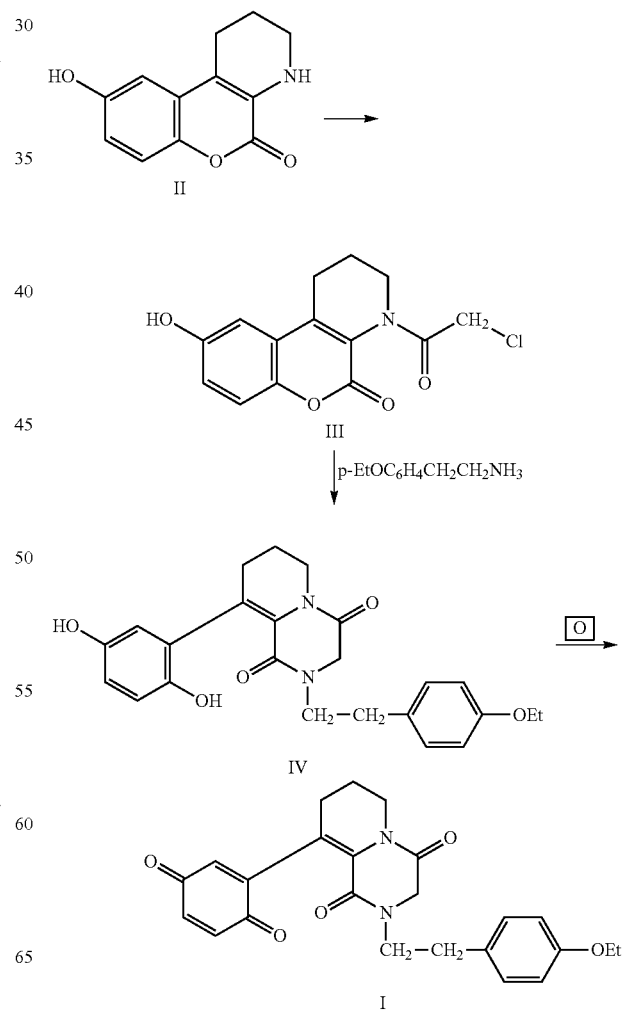

Synthesis of III:

7.7 ml (95 mmol) of chloroacetyl chloride are added, stirring continuously, into a suspension of 4.23 g (19 mmol) chromene in 35 ml of toluene, boiled for 1 hour, cooled down, filtered 5.47 g III (yield 98%), m.p. 162° C. (EtOH). $^1$H NMR (DMS-d$_6$, δ) 2.01 (q, 2H), 2.89 (t, 2H), 3.71 (br.s, 2H), 4.38 (s, 2H), 7.03 (m, 2H), 7.26 (d, 1H), 9.60 (s, 1H).

Synthesis of IV:

12 mmol β-(p-ethoxyphenyl)ethylamine is added to the solution of 0.88 g (3 mmol) III in 6 ml of dimethylformamide, stirred for 1 hour under 20° C., diluted by water, filtered 1 g IV, yield 93%, m.p. 169-171° C. (MeCN).

Synthesis of I.

A solution of 0.14 sodium bicarbonate in 2.5 ml of water and oxidizing mixture of 0.6 g K$_3$[Fe(CN)$_6$], 0.14 g NaHCO$_3$ and 0.18 g K$_2$CO$_3$ in 6 ml water are added into a suspension of 1 mmol IV in 10 ml chloroform. The mixture is stirred for 1 hour under 20° C., the organic layer is separated and evaporated, the residue is grinded with ether, yielding 85% I, m.p. 137-140° C. Found: C 68.36, H 6.12, N 6.57. Calcd for $C_{24}H_{24}N_2O_4$: C 68.56, H 5.75, N 6.66. $^1$H NMR (DMS-d$_6$, δ) 1.32, 4.25 (t and q, 3H and 2H, $CH_3CH_2$, J=7.5 Hz), 1.86 (quint, 2H, 7-$CH_2$, J=7.5 Hz), 2.34 (br.s, 2H, 8-$CH_2$), 2.68 и 3.40 (both t, 2H, 2-$CH_2CH_2$, J=7.2 Hz), 4.04 (s, 2H, 3-$CH_2$), 6.68 (d, 1H, J=2.8 Hz), 6.78 (quint, 1H, 4'-H), 6.89 (quint, 1H, 5'-H, J=8.4 Hz), 6.80-7.10 (AA'BB', 4H, $C_6H_4$).

Compounds containing, for example, cyclodextrins may be used as pharmaceutically acceptable complex compounds. New compounds possess antisecretory and gastroprotective activity.

EXAMPLE I

Antiulcer action of compound I was studied in next models:

1.1. Gastric mucosa damage in mice, induced by the administration of 0.6 N hydrochloric acid and indomethacin [13].

Male mice (body mass 23-24 g) were deprived of food for 24 hours while allowing water. The studied compound was administered in 25, 50 and 100 mg/kg doses by a tube into the stomach 1, 3 and 6 hours before the administration of 0.6 N hydrochloric acid (5 ml/kg doses) and indomethacine (20 mg/kg doses), after an hour the animals were sacrificed, their stomachs were extracted, the number of ulcers was studied. Famotidine in 25 and 50 mg/kg doses and omeprazole in 50 mg/kg dose were chosen as drugs of comparison.

1.2. Model of gastric mucosa damage, induced by the administration of absolute ethanol [14]. Male rats (body mass 20-23 g) were deprived of food 24 hours before the experiment and of water 18 hours before the experiment. The studied compound was administered in 25, 50 and 100 mg/kg doses by a tube into the stomach 1, 3 and 6 hours before the administration of absolute ethanol (0,3 ml), after that the animals were sacrificed, their stomachs were extracted and the length of ulcerations was measured in millimeters.

The experiments also used control animals that received only 0.3 ml of saline. Famotidine in 25 and 50 mg/kg doses and omeprazole in 50 mg/kg dose were chosen as drugs of comparison.

1.3. Model of gastric mucosa damage, induced by the administration of the compound 48/80 [15].

The studied compound was administered in 25 and 100 mg/kg by stomach tube 1 and 6 hours before the intraperitoneal administration of compound 48/80, the damage to gastric mucous membranes was observed 3 hours afterwards by sacrificing animals, extracting their stomachs and measuring the length of ulcers in millimeters. Famotidine in 25 and 50 mg/kg doses and omeprazole in 50 mg/kg dose were chosen as drugs of comparison.

1.4. Model of chronic stomach ulcer, induced by the administration of 0.025 ml 20% acetic acid to rats [16].

Chronic gastric ulcer was induced in rats by administering 0.025 ml of 20% acetic acid under the stomach serous membrane into the border between the antrum and fundus. 24 hours after the operation the studied compound in 50 mg/kg dose and drugs of comparison (omeprazole-50 mg/kg and famotidine—50 mg/kg) started to be administered by a tube into the stomach once a day during 21 days. Every 7 days 6 animals from control and test groups were sacrificed and the surface of stomach ulceration was measured in mm$^2$.

EXAMPLE II

Studying Antisecretory Activity 2.1. Studying the influence of the compound on basal secretion in rats [17].

The study was conducted using male rats weighting 180-200 g. The animals were deprived of food for 24 hours, water access was not limited. Using ether anesthesia their abdomens were opened and a ligature put on the pylorus. 4 hours after the operation stomach contents were studied: secretion volume per 100 g of animal mass, gastric acid pH, free hydrochloric acid and general acidity of gastric acid. The studied compound was administered in 100 mg/kg dose as water suspension, with the addition of Tween-80, 60 minutes before the ligature of pylorus. Control animals were given distilled water with the addition of Tween-80. Omeprazole in 50 mg/kg dose and famotidine in 25 and 50 mg/kg doses were used as drugs of comparison.

2.2. Studying gastric secretion stimulated by histamine, pentagastrin and 1-aminopyrene.

The study was conducted using male rats weighting 180-200 g. The animals were deprived of food for 24 hours, water access was not limited. Before putting a ligature on the pylorus, one group of animals was administered histamine (2.5 mg/kg) subcutaneously, second group was administered pentagastrin (10 mg/kg) subcutaneously, third group was administered 1-aminopyrene 1 mg/kg. The studied compound was administered in 100 mg/kg dose as water suspension, with the addition of Tween-80, 1 and 3 hours before the ligature of pylorus. Control animals were given distilled water with the addition of Tween-80. Omeprazole in 50 mg/kg dose and famotidine in 25 and 50 mg/kg doses were used as the drugs of comparison. 4 hours after the operation stomach contents were studied: secretion volume per 100 g of animal mass, gastric acid pH, free hydrochloric acid and general acidity of gastric acid.

EXAMPLE III

Peristalsis Study 3.1. Studying intestinal peristalsis [18].

The studied compounds were administered to male mice (body weight 22-24 g) by a tube into the stomach 60 minutes before the administration of activated charcoal (0.3 ml of 10% suspension into the stomach). After 2 hours the animals were sacrificed by CO2 and the length of small intestine filled with charcoal was measured in cm. Control group animals were administered 0.3 ml of water, cerucal in 25 mg/kg dose was chosen as the drug of comparison.

EXAMPLE IV

Studying the Toxicity (LD50) of Studied Compounds Following Single Administration [19]

Results of Studies

1. It was shown that piperazindione derivatives exhibit gastroprotective action towards ulcers induced by absolute ethanol, voltaren, compound 48/80, and also exhibits antiulcer action by enhancing ulcer healing in the model of chronic gastric ulcer induced by acetic acid. They are more effective than famotidine and are as potent as omeprazole. Their time of action is equal to omeprazole and famotidine, no prolonged action was noted.

2. Studies of antisecretory action have shown that omeprazole inhibits basal secretion by 25% one hour after administration and by 40% after three hours; famotidine: by 56% after 1 hour and by 80% after 3 hours. Unlike known antiulcer drugs (proton pump inhibitors, $H_2$ receptor antagonists) the new compound does not inhibit basal gastric acid secretion level.

Thus, famotidine severely inhibits basal secretion, omeprasol—moderately. The new compound does not inhibit basal secretion level at all.

3. Studies of stimulated gastric acid secretion have shown that omeprazole inhibits histamine-induced secretion by 70% one hour after administration, and by 80% after 3 hours; pentagastrin-induced and 1-aminopyrene-induced secretion—by about 90%. Famotidine inhibits histamine-induced secretion by 90% one hour after administration, and by 95% after 3 hours; pentagastrin-induced secretion by 40% and 1-aminopyrene-induced secretion—by 36% after 1 hour and by 40% after 3 hours. The new compound inhibits histamine-induced secretion by 40% one hour after administration, and by 57% after 3 hours; pentagastrin-induced secretion by about 54% and 1-aminopyrene-induced secretion by 50%.

Thus, omeprazole inhibits gastric acid secretion induced by all three substances (histamine, pentagastrin, 1-aminopyrene), famotidine inhibits only histamine-induced secretion, and weakly inhibits secretion caused by two other substances, the studied compound, like omeprazole, inhibits all three types of stimulated secretion, but less potently.

4. Peristalsis study has shown that omeprazole slows down intestinal peristalsis by 35%, famotidine does not influence peristalsis, the new compound does not influence peristalsis as well.

Thus, only omeprazole inhibits intestinal peristalsis. This effect may be detrimental to its antiulcer activity, especially during long-term use, because inhibition of peristalsis causes stomach contents to exhibit additional deleterious effect on ulcers.

General toxicity studies have shown that the new compound and its salts are low-toxic, like omeprazole. Comparison of LD50 has shown that new compounds are less toxic than famotidine and omeprazole.

EXAMPLE 5

Study of Compound I Action on Enzyme Activity of H,K-Atpase of Rabbit Gastric Mucosa, its Reversibility and Potency in the Presence of K+ Ions Microsome preparation, enriched with H+, K+-ATPase, was produced from the rabbit stomach mucosa using a method proposed by Farley and Faller.

Gastric mucosa was produced from a decapitated rabbit. All operations were carried out in ice. The stomach was cut at the greatest curve line, washed and scrubbed. Obtained mucosa was frozen and kept at −80° C. temperature.

To obtain a microsome preparation enriched with H,K-ATPase, gastric mucosa was defrozen and homogenized in extraction medium (0.25 mol sucrose, 5 mmol PIPES, 20 mmol Tris (THAM), ph 7.4) by a Polytron-class homogenizer (max rotations 30/sec). Mass ratio of tissue to extraction medium—1:20.

The homogenate was then centrifuged for 10 min at 10000 g. The sediment was discarded and supernatant was them centrifuged for 1 hour at 100000 g. The produced sediment was re-suspended in extraction medium (using the minimal volume necessary for re-suspension). The suspension was layered above Ficoll 400, prepared in the extraction medium: 12% Ficoll solution, 4% Ficoll solution. It was further centrifuged for 180 min at 100000 g. After centrifuging, a white layer was seen on the borderline of 4% and 12% Ficoll that was a microsome fraction, enriched with H,K-ATPase. The fraction was collected, divided into aliquots and kept at −80° C.

The effect was measured by the growth of inorganic phosphate that is produced during ATP hydrolysis. The concentration was measured using Ratbun and Betlah method. The incubation medium contained: 30 mmol imidazole, ph 7.4, 3 mmol MgCl2, 130 mmol NaCl, 20 mmol KCl, 3 mmol ATP, 2 mmol ouabain, 0.1 mmol EGTA, 2.25 μmol valinomycin, 5 mmol NaN3, 5 μmol of CCCP (Carbonyl cyanide m-chlorophenyl hydrazone).

Incubation medium and defrozen and homogenized microsome fraction were added into incubation sample. The sample was incubated for 20 min at 37° C., then the reaction was stopped by a cold stop-solution (3 mol sodium acetate, 3.7% formaldehyde, pH 4.3).

To evaluate the content of phosphate, produced during enzymatic hydrolysis of ATP, 2% ammonium molybdate solution and tin chloride solution (3 mg/ml) was into the sample. After the appearance of blue color, after 15 minutes, the samples were studied by colorimetry using wavelength of 650 nm The H,K-ATPase activity was determined as activity inhibited by 0.1 mmol SCH-28080. This inhibitor inhibited about 30% of H,K-ATPase activity. The concentration of the studied compound was varied in range of $10^{-8}$ to $10^{-4}$ mol.

Results of Studies

Compound I exhibits inhibitory action on H,K-ATPase activity of rabbit gastric mucosa with I50=10−6 M. Its effect on H,K-ATPase is reversible, it develops instantly and stops after the dilution of enzyme-inhibitor complex.

Possible competition between compound I and potassium ions was studied. To achieve this, the relation of H,K-ATPase and KCl concentration was studied, and then the inhibitory action of compound I on this enzyme in saturated (20 μmol) and unsaturated (2 μmol) concentrations of KCl was studied.

It was shown that Compound I does not compete with K+ ions, on the contrary, its inhibitory effect of rabbit mucosa H,K-ATPase became more potent in the presence of K+ ions: $I_{50}$ was $10^{-5}$ mol at 2 μmol KCl and $10^{-6}$ at 20 μmol KCl.

Conclusions

1. Compound I reversibly inhibits the hydrolytic activity of H,K-ATPase, $I_{50}$ is 20 μmol KCl.

2. Inhibitory effect of Compound I becomes more potent in high K+ concentrations. $I_{50}$ goes down from $10^{-5}$ mol at 2 μmol KCl to $10^{-6}$ mol at 20 μmol KCl. This property of Compound I is an advantage in living organism use.

Results show that Compound I is an effective reversible H,K-ATPase inhibitor. But, unlike the known reversible inhibitor SCH-28080, Compound I is not competitive in relation to potassium. It seems that Compound I does not bind to K-binding site of the enzyme. Moreover, K+ enhances the inhibitory effect of Compound I. This may be important regardless of whether the inhibitor acts via cytoplasm or via secretory vesicles, because K+ concentration may reach high levels even in secretory vesicles, which are directly linked to stomach cavity. This shows that Compound I is a new hitherto unknown class of reversible H,K-ATPase inhibitors, with a mechanism of action not competitive in relation to $K^+$.

REFERENCES

1. El-Matary W., Dalzell M. "Omeprazole-induced hepatitis" // Pediatr. Emerg. Care, 2005, V. 21(8): 529-530.
2. Raghunath A. S., O'Morain C, McLoughlin R. C. "Review article: the long-term use of proton-pump inhibitors" // Aliment Pharmacol. Ther., 2005 V. 22, Suppl. 1:55-63.
3. Reilly J. P. "Safety profile of the proton-pump inhibitors" // Best Pract. Res. Clin. Gastroenterol., 2001, V 15 (3): 355 370.
4. Clissold S. P. and Campoli-Richards D. M. "Omeprazole: A preliminary review of its pharmacodynamic and pharmacokinetic properties, and therapeutic potential in peptic ulcer disease and Zollinger-Ellison syndrome" // Drugs, 1986, V. 32: 15-47.
5. Katz, L. B., Shriver, D. A. "Rioprostil heals pre-existing aspirin-induced gastric lesions in dogs during daily aspirin administration without altering the anti-inflammatory or analgesic efficacy of aspirin"//J. Pharmacol. Exp. Ther., 1989, 251(2): 774.
6. Esplugues J. V., Calatayund S., Beltran B. et al. "Role of nitric oxide in gastric functions" // Meth. And Find. Exp. And Clin. Pharmacol., 1997, V. 19 A, 25-27.
7. Cuzzolin L., Adami A., Crivellente F. et al. "Role of endogenous and exogenous nitric oxide on intestinal mucosa and microflora in the rat" // Inflammation, 1997, V. 21, N 4: 443-450.
8. Yoshimura-Mishima, M., Akamatsu, H., Adachi, Y., Horio, T., <<Suppressive effect of Oren-gedoku-to (Huang-Li and Jie-Du-Tang) on the production of superantigen by *Staphylococcus aureus*>> //Jpn. Pharmacol. Ther., 2002, 30(3): 225.
9. Ido, T. et al Inhibitory effect of Oren-gedoku-to (TJ-15) on gastric mucosal injury induced by compound 48/80 Jpn. J. Pharmacol., 1999, 79 (Suppl. I) Abst P-24.
10. Hayashi, T. et al Inhibitory action of Oren-gedoku-to extract on enzymatic lipid peroxidation in rat liver microsomes. Biol. Pharm. Bull., 2001, 24(10): 1 165.
11. Saha, J. K., Wang, T., Glavin, A., Chen, L., Garvey, D. S., Letts, L. G., Tarn, S. W. Nitric-oxide donating $H_2$-receptor antagonist and proton pump inhibitor with enhanced antiulcerogenic activities in rats FASEB J, 2000, 14(8) Abst 1399.
12. Saha, J., et al. Enhanced gastroprotective and anti-ulcerogenic activities in rats of a new class of proton pump inhibitor containing nitrosothiol nitric oxide donor Dig Dis Week (May 20-23, Atlanta) 2001, Abst 772.
13. Yano S., Harada M., Watanabe K. et al. "Antiulcer activities of glycyrrhetinic acid derivatives in experimental gastric lesion models" // Chem. Pharm. Bull. (Tokyo), 1989, V. 37, N 9, P. 2500-2504.
14. Derelanko M., Long J. "Carbenoxolone Sodium protects rat gastric mucosa against Ethanol-induced necrosis" // Proc. Soc. Exp. Biol. Med., 1981, V. 166, N 3, P. 394-397.
15. Ohta Y., Obayashi T., Inui et al. "Protective effect of teprenone against acute gastric mucosal lesions induced by compound 48/80, a mast cell degranulator, in rats" // J. Pharmacol. Sci., 2003, V. 93: 337-346.
16. Shay H., Komarov S., Fels S., et al. "A simple methods for the uniform production of gastric ulceration in the rat" // Gastroenterology, 1945, N 5, P. 43-61.
17. Janssen P., Jageneau A. "Research papers a new series of potent analgesics: dextro 2;2; diphenyl-3-methyl-4-moholino-butyryl-pyrrolidine and related amides" // J. Pharm. Pharmacol., 1957, V. 9, P. 381-399.
18. Belenky M. L. Elements of quantitative evaluation of pharmacological effect. Leningrad, 1963.
19. Kaminski J., et al. Antiulcer agents 5 Inhibition of gastric $H^+/K(^+)$-ATPase by substituted imidazo [1,2-a]pyridines and related analogues and its implication in modeling the high affinity potassium ion binding site of the gastric proton pump enzyme. J. Med. Chem., 1991 February; 34(2): 533-41.
20. Sachs G., Shin, J. M, Vagin, O., Lambrecht, N., Yakubov, I, Munson K. (2007) The gastric H,K-ATPase as a drag target: past, present, and future. J. Clin. Gastroenterol., 41 (6 Suppl 2): P. 226-242.
21. Vagin, O., Munson K., Denevich, S., Sachs, G., SCH28080, a K+-competitive inhibitor of the gastric H,K-ATPase, binds near the M5-6 luminal loop, preventing K+ access to the ion binding domain. Biochemistry., 2002 41(42): 12755-12762.

What is claimed is:

1. A compound comprising 9-(quinonil-2)-2-p-ethoxyphenylethyl-4,5,6,7,8,9,10,11-octahydropyrido[1,2-a]pyrazindione-1,4 of formula (I)

I

2. The compound according to claim 1, possessing reversible inhibitory effect on H,K-ATPase.

3. The compound according to claim 1, exhibiting antisecretory and gastroprotective activity.

4. A method for the treatment of gastric ulcer in a mammal, comprising administering to said mammal a therapeutically effective amount of a compound comprising 9-(quinonil-2)-2-p-ethoxyphenylethyl-4,5,6,7,8,9,10,11-octahydropyrido [1,2-a]pyrazindione-1,4 of formula (I)

I or its pharmaceutically acceptable complex derivatives.

5. The method of claim 4, wherein the therapeutically effective amount of the compound is suitable for peroral, parenteral or topical administration.

6. The method of claim 4, wherein administering to the mammal a single dose of the therapeutically effective amount of the compound ranging from about 1 mg to about 500 mg comprises administering the single dose of the compound as stand-alone drug therapy or as a component of combination therapy.

* * * * *